(12) United States Patent
Okiyama

(10) Patent No.: US 9,775,979 B2
(45) Date of Patent: Oct. 3, 2017

(54) MALE CONNECTOR EQUIPPED WITH LOCK MECHANISM

(71) Applicant: JMS CO., LTD., Hiroshima-shi, Hiroshima (JP)

(72) Inventor: Tadashi Okiyama, Hiroshima (JP)

(73) Assignee: JMS CO., LTD, Hiroshima (JP)

( * ) Notice: Subject to any disclaimer, the term of this patent is extended or adjusted under 35 U.S.C. 154(b) by 17 days.

(21) Appl. No.: 14/391,349

(22) PCT Filed: Apr. 5, 2013

(86) PCT No.: PCT/JP2013/060493
§ 371 (c)(1),
(2) Date: Oct. 8, 2014

(87) PCT Pub. No.: WO2013/154049
PCT Pub. Date: Oct. 17, 2013

(65) Prior Publication Data
US 2015/0105753 A1    Apr. 16, 2015

(30) Foreign Application Priority Data
Apr. 13, 2012   (JP) ................. 2012-092292

(51) Int. Cl.
*A61M 39/04*   (2006.01)
*A61M 39/12*   (2006.01)
*A61M 39/10*   (2006.01)

(52) U.S. Cl.
CPC ...... *A61M 39/045* (2013.01); *A61M 39/1011* (2013.01); *A61M 39/12* (2013.01);
(Continued)

(58) Field of Classification Search
CPC .... A61M 39/04; A61M 39/045; A61M 39/10; A61M 39/1011; A61M 39/12;
(Continued)

(56) References Cited

U.S. PATENT DOCUMENTS 5,122,123 A * 6/1992 Vaillancourt ......... A61M 39/14
604/192
5,496,274 A * 3/1996 Graves ............... A61M 39/1011
604/192
(Continued)

FOREIGN PATENT DOCUMENTS

FR    2 931 363    11/2009
JP    2549223 B    10/1996
(Continued)

OTHER PUBLICATIONS

Extended European Search Report issued in corresponding European Application, dated Jun. 17, 2016, 6 pages.

*Primary Examiner* — Nathan R Price
*Assistant Examiner* — Justin L Zamory
(74) *Attorney, Agent, or Firm* — Hamre, Schumann, Mueller & Larson, P.C.

(57) ABSTRACT

A lock mechanism includes a hood (20) that is arranged so as to surround the periphery of a male member (10) and is for insertion of a female connector (100), and a single lock lever (30) having a cantilever support structure capable of elastic displacement. The lock lever (30) includes a claw (34) for engaging with the female connector (100), and an operation portion (35) for elastically displacing the lock lever (30) in a direction of separation from the male member (10). The claw (34) and the operation portion (35) are provided on the free end side of the lock lever (30).

7 Claims, 10 Drawing Sheets

(52) U.S. Cl.
CPC ............... *A61M 2039/1016* (2013.01); *A61M 2039/1027* (2013.01)

(58) Field of Classification Search
CPC .. A61M 2039/1016; A61M 2039/1027; A61M 2039/1072
USPC ................................ 604/523, 533, 534, 535
See application file for complete search history.

(56) References Cited

U.S. PATENT DOCUMENTS

| | | | |
|---|---|---|---|
| 5,582,600 | A | 12/1996 | Loh |
| 5,964,785 | A | 10/1999 | Desecki et al. |
| 6,213,996 | B1 | 4/2001 | Jepson et al. |
| 6,290,688 | B1 * | 9/2001 | Lopez ................ A61M 39/1011 604/500 |
| 6,468,251 | B1 | 10/2002 | Yamanaka et al. |
| 2004/0243065 | A1 | 12/2004 | McConnell et al. |
| 2011/0175347 | A1 | 7/2011 | Okiyama |
| 2011/0178493 | A1 | 7/2011 | Okiyama |
| 2012/0286186 | A1 * | 11/2012 | Spolski ......................... 251/367 |

FOREIGN PATENT DOCUMENTS

| | | |
|---|---|---|
| JP | 2002-528234 | 9/2002 |
| JP | 3389983 B | 3/2003 |
| JP | 2004-000483 | 1/2004 |
| JP | 2008-000331 | 1/2008 |
| JP | 2012-034738 | 2/2012 |
| WO | 2010/061742 | 6/2010 |
| WO | 2010/061743 | 6/2010 |
| WO | 2011/145991 | 11/2011 |

* cited by examiner

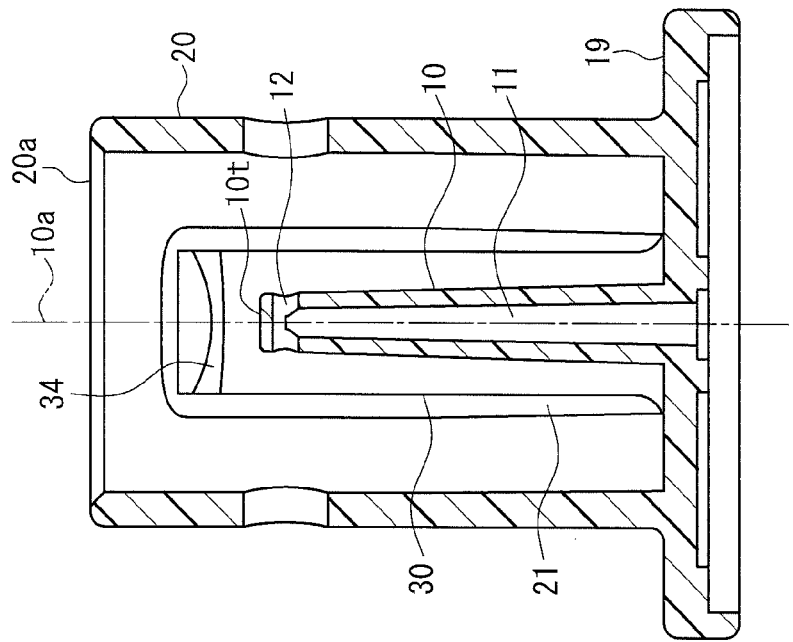
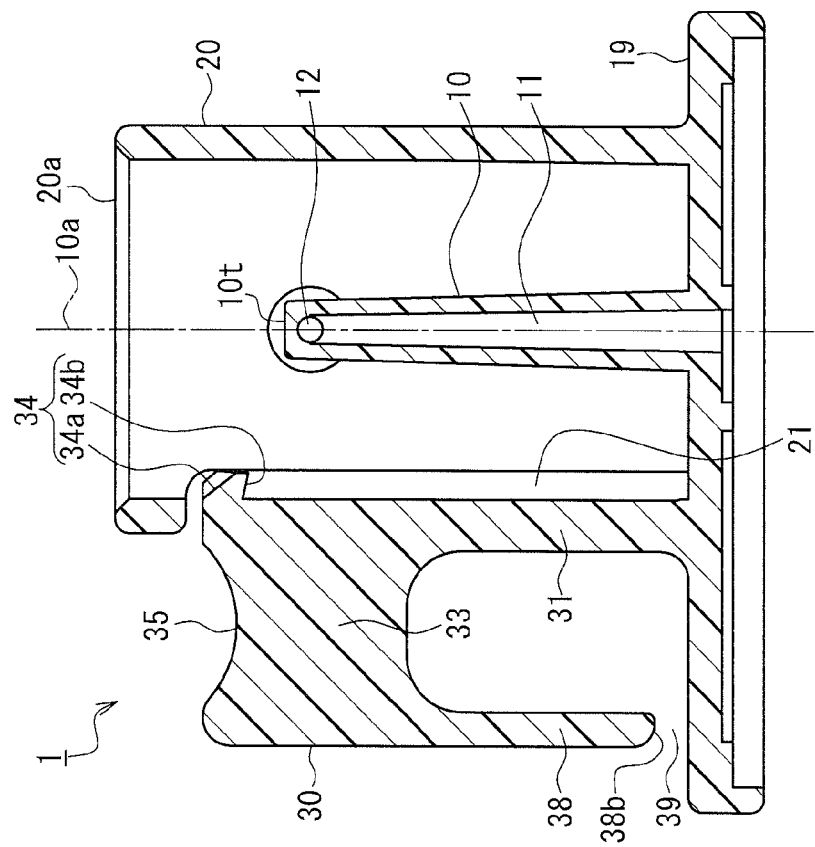
FIG. 3A
FIG. 3B

MALE CONNECTOR EQUIPPED WITH LOCK MECHANISM

TECHNICAL FIELD

The present invention relates to a male connector that includes a lock mechanism for maintaining a state of connection to a female connector.

BACKGROUND ART

When giving a patient an infusion or blood transfusion or performing extracorporeal blood circulation in surgery, it is necessary to form a channel (transport line) for transporting a liquid such as a drug solution or blood. Transport lines generally are formed by connecting containers, various types of instruments, feed tubes, and the like. Also, when a drug solution to be administered to a patient is injected into a drug solution bag (container), it is necessary to connect the drug solution bag and a syringe or the like. In this way, a male connector and a female connector are used to interconnect different members detachably.

One known example of a female connector used in this application is a needleless port that has a disk-shaped partition wall member (hereinafter referred to as a "septum") that is made of an elastic material such as rubber and has a linear slit (incision) formed in the central portion (e.g., see Patent Document 1). By inserting a tubular male luer (male member), which does not have a sharp metal needle such as an injection needle attached thereto, into the slit in the septum, the needleless port and the male luer can be put in communication with each other. The slit in the septum immediately closes when the male luer is withdrawn from the needleless port.

There are cases where the drug solution contains a drug designated as a dangerous drug, such as some anticancer drugs. There are also cases where blood contains a pathogen or the like. Accordingly, it is necessary to avoid a situation where a connected male connector and female connector unintentionally become separated, and as a result a liquid such as a drug solution or blood leaks out and comes into contact with the operator's finger or the like, or the operator inhales vapor from the liquid.

In view of this, a male connector with a lock mechanism 900 has been proposed in which, as shown in FIGS. 9A and 9B, a male luer 910 is provided with a lock mechanism for maintaining a state in which the male luer 910 is connected to a needleless port (e.g., see Patent Documents 2 to 4). This lock mechanism includes a pair of lock levers 930 arranged so as to be approximately parallel to the male luer 910 and sandwich the male luer 910. The lock levers 930 are connected to a base end portion 919 of the male luer 910 via support pieces 931 provided at an approximately central position in the lengthwise direction of the lock levers 930. A claw 934 that engages with the needleless port is formed on one end of each of the lock levers 930, on the surface on the side that opposes the male luer. The end portions of the lock levers 930 on the side not provided with the claws 934 are operation portions 935 for operating the lock levers. When the operation portions 935 of the pair of lock levers 930 are pressed toward each other, the support pieces 931 undergo elastic deformation, and the lock levers 930 become displaced in the direction in which the claws 934 move away from the male luer 910. Numeral 920 indicates an approximately cylindrical hood that surrounds the male luer 910 and is fixed to the base end portion 919. The pair of lock levers 930 are arranged in notches provided in the hood 920.

Numeral 915 indicates a tubular portion that is in communication with the male luer 910 and is for connection to a flexible tube (not shown).

As shown in FIG. 10, the male luer 910 is inserted into a septum 951 of a needleless port 950, and the claws 934 provided on the tips of the pair of lock levers 930 are engaged with a step on the outer circumferential face of the needleless port 950. Accordingly, the state of connection of the needleless port 950 and the male luer 910 is locked. Even if the male connector 900 and the needleless port 950 are pulled away from each other, the male connector 900 and the needleless port 950 cannot be separated since the claws 934 of the lock levers 930 are engaged with the needleless port 950. The male connector 900 and the needleless port 950 can be separated by applying force F1 to the operation portions 935 of the pair of lock levers 930 in a direction in which they approach each other, so as to displace the lock levers 930 and cancel the engagement between the claws 934 of the lock levers 930 and the needleless port 950.

PRIOR ART DOCUMENTS

Patent Document

[Patent Document 1] JP 3389983B
[Patent Document 2] JP 2004-483A
[Patent Document 3] WO 2010/061742
[Patent Document 4] WO 2010/061743

DISCLOSURE OF INVENTION

Problem to be Solved by the Invention

With the above-described conventional lock mechanism including the pair of lock levers 930, the locked state can be canceled by applying the pressing force F1 to the operation portions 935 of the lock levers 930. Accordingly, if an unintended external force is applied to the operation portions 935 of the lock levers 930, there is a possibility of the locked state becoming canceled.

An object of the present invention is provided a male connector with a lock mechanism that is highly safe and has a reduced possibility of the locked state being unintentionally canceled by external force.

Means for Solving Problem

A male connector with a lock mechanism of the present invention includes a bar-shaped male member for insertion into a female connector, and a lock mechanism for maintaining a state in which the male member is inserted into the female connector. The lock mechanism includes a hood that is arranged so as to surround a periphery of the male member and is for insertion of the female connector, and a single lock lever having a cantilever support structure capable of elastic displacement. The lock lever includes a claw for engaging with the female connector, and an operation portion for elastically displacing the lock lever in a direction of separation from the male member. The claw and the operation portion are provided on a free end side of the lock lever.

Effects of the Invention

According to the lock mechanism of the present invention, the claw provided on the single lock lever can be engaged with the female connector inserted into the hood, thus making it possible to maintain the state in which the male member is connected to the female connector. Also, canceling the engagement between the claw and the female connector requires displacing the lock lever in the direction of moving away from the male member, and thus there is a low possibility of the locked state achieved by the lock mechanism being unintentionally canceled by external force. Accordingly, it is possible to provide a male connector with a lock mechanism that is highly safe.

BRIEF DESCRIPTION OF DRAWINGS

FIG. 3A is a cross-sectional arrow view of the male connector with a lock mechanism according to the embodiment of the present invention taken along a plane including a line 3A-3A in FIG. 2A.

FIG. 3B is a cross-sectional arrow view of the male connector with a lock mechanism according to the embodiment of the present invention taken along a plane including a line 3B-3B in FIG. 2A.

DESCRIPTION OF THE INVENTION

Figure 1:
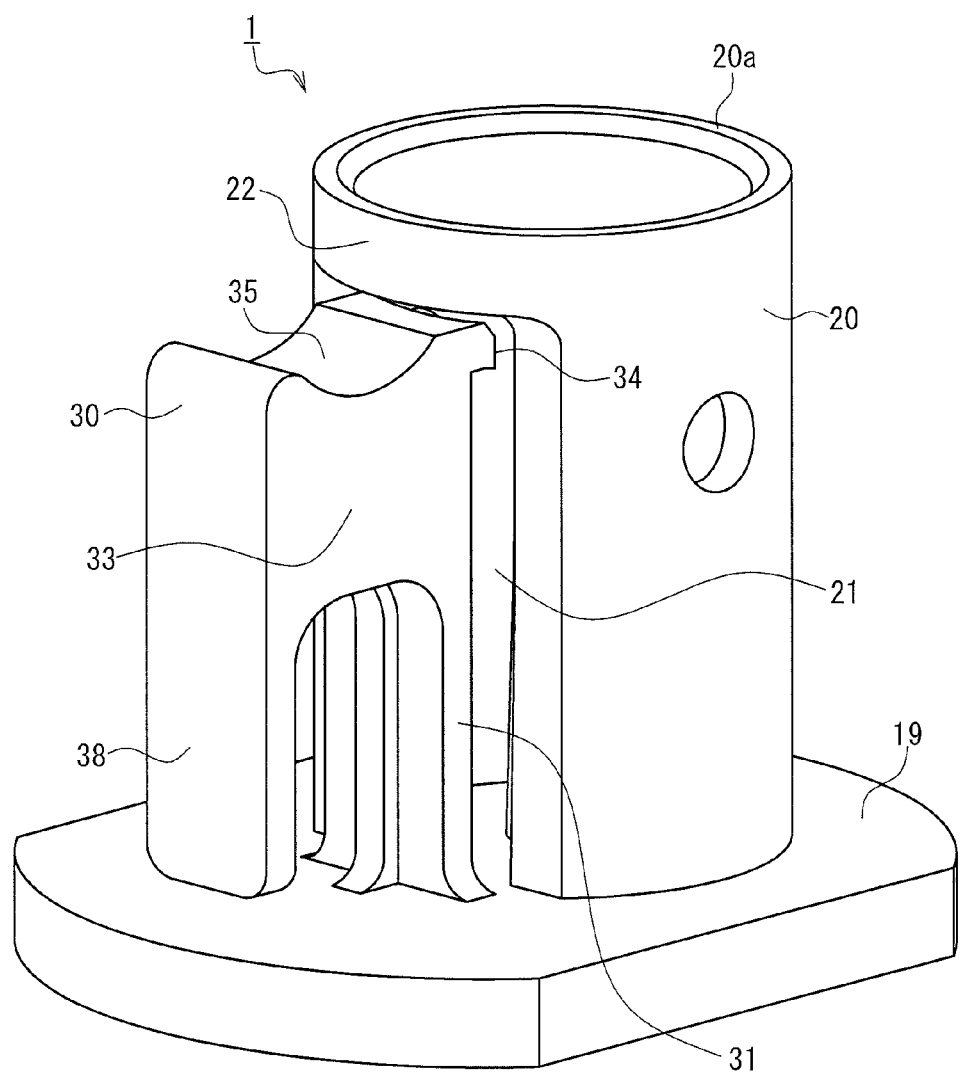
FIG. 1 is a perspective view of a male connector with a lock mechanism according to an embodiment of the present invention.

A male connector with a lock mechanism of the present invention includes a bar-shaped male member for insertion into a female connector, and a lock mechanism for maintaining a state in which the male member is inserted into the female connector. The lock mechanism includes a hood that is arranged so as to surround a periphery of the male member and is for insertion of the female connector, and a single lock lever having a cantilever support structure capable of elastic displacement. The lock lever includes a claw for engaging with the female connector, and an operation portion for elastically displacing the lock lever in a direction of separation from the male member. The claw and the operation portion are provided on a free end side of the lock lever.

It is preferable that the above male connector with a lock mechanism of the present invention further includes a displacement limiting means that sets an upper limit of an elastic displacement amount of the lock lever. According to this, it is possible to prevent the lock lever from becoming plastically deformed or damaged due to an operator greatly displacing the lock lever more than necessary.

It is preferable that an opening for allowing engagement of the claw to the female connector is formed in the hood. Compared to a configuration in which the height of the hood is reduced or a notch is formed in the upper edge of the hood, this preferable configuration is advantageous in preventing an operator from mistakenly touching the male member, in positioning the female connector using the hood, and in suppressing a reduction in the mechanical strength of the hood.

It is preferable that the hood includes a bridge portion on a side on which the female connector is inserted relative to the opening, and the bridge portion connects portions of the hood that sandwich the opening in a circumferential direction. According to this, even if external force acts on the female connector in the state of being connected and locked to the male connector, it is possible to suppress inclination and movement of the female connector. As a result, it is possible to reduce the possibility of the locked state being unintentionally canceled and the hood becoming damaged.

It is preferable that a channel is formed in the male member, and a lateral hole in communication with the channel is open at an outer circumferential face of the male member. When the male member that has been inserted into the female connector is withdrawn from the female connector, liquid attached to the periphery of the opening of the lateral hole is scraped away by the female connector, and therefore according to the above configuration, it is possible to reduce the amount of liquid that remains in the periphery of the opening of the lateral hole after withdrawal from the female connector.

The present invention will be described below in detail while disclosing preferred embodiments. However, it goes without saying that the present invention is not limited to the following embodiments. For the sake of convenience in the description, the drawings that are referenced in the following description show simplifications of, among the constituent members of the embodiment of the present invention, only the relevant members that are necessary for describing the present invention. The present invention therefore can include arbitrary constituent members that are not shown in the following drawings. Also, regarding the dimensions of the members in the drawings, the dimensions of the actual constituent members, the ratios of the dimensions of the members, and the like are not shown faithfully.

Figure 2A:
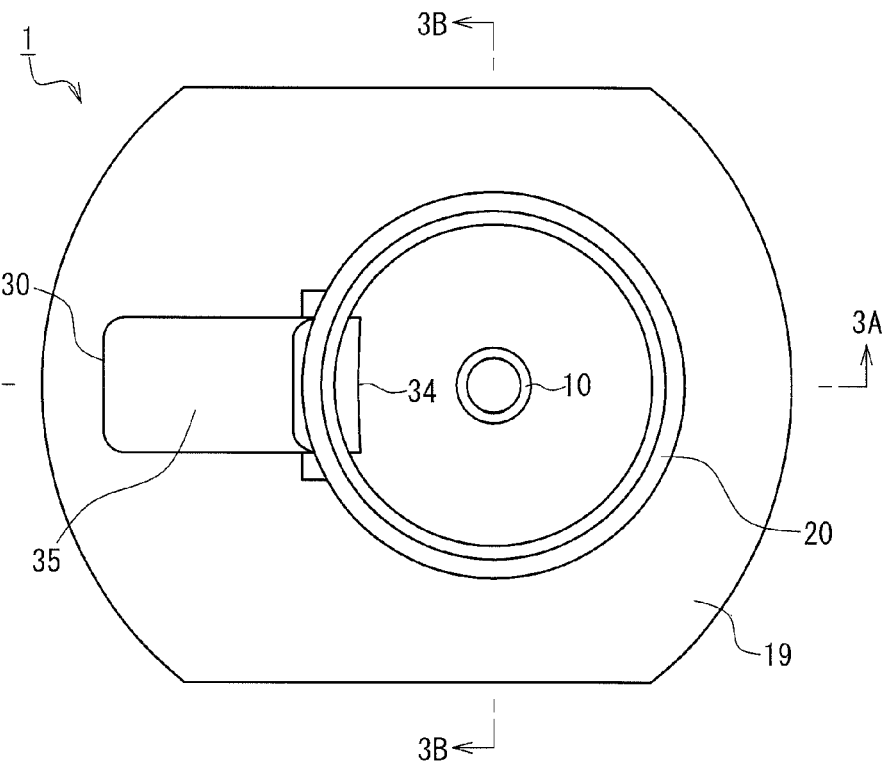
FIG. 2A is a plan view of the male connector with a lock mechanism according to the embodiment of the present invention.
Figure 2B:
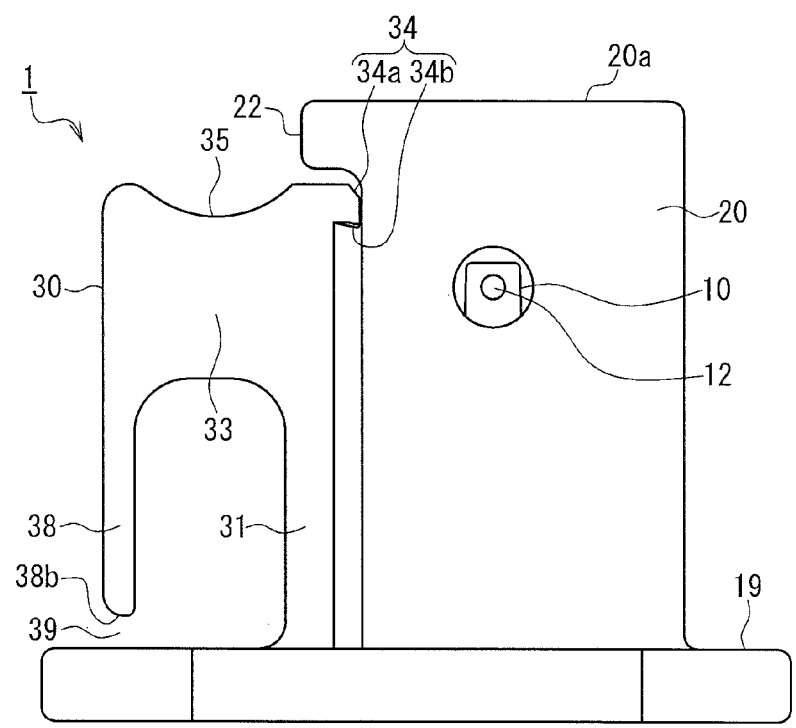
FIG. 2B is a side view of the same.

FIG. 1 is a perspective view of a male connector with a lock mechanism (referred to hereinafter as simply "male connector") 1 according to an embodiment of the present invention. FIG. 2A is a plan view of the male connector 1, and FIG. 2B is a side view of the male connector 1. Furthermore, FIG. 3A is a cross-sectional arrow view of the male connector 1 taken along a plane including a line 3A-3A in FIG. 2A, and FIG. 3B is a cross-sectional arrow view of the male connector 1 taken along a plane including a line 3B-3B in FIG. 2A.

Figure 10:
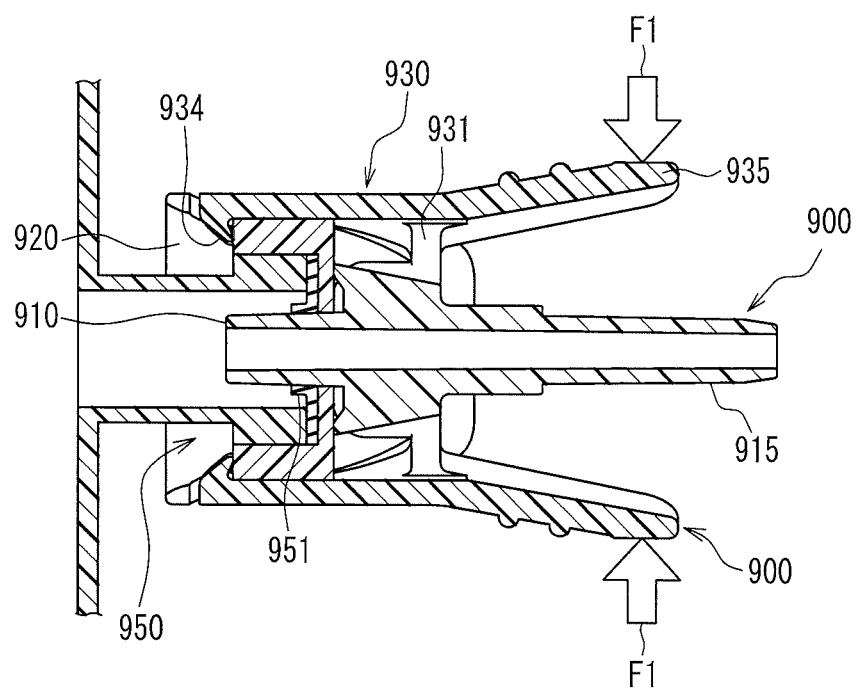
FIG. 10 is a cross-sectional view of the conventional male connector with a lock mechanism when connected to a needleless port.

The male connector 1 of the present embodiment includes a bar-shaped male luer 10 as a male member. In FIGS. 3A and 3B, 10a indicates the central axis of the male luer 10. For convenience in the following description, the lengthwise direction of the male luer 10 (direction parallel to the central axis 10a) will be referred to as the "up-down direction", and the direction orthogonal to the lengthwise direction of the male luer 10 will be referred to as the "horizontal direction". Also, with regard to the up-down direction, the side close to a base 19 will be referred to as the "lower side", and the side far from it will be referred to as the "upper side" or the "tip side". Note that the "up-down direction" and the "horizontal direction" do not mean orientations during actual use of the male connector 1. Furthermore, the direction of a line orthogonal to the central axis 10a of the male luer 10 will be referred to as the "radial direction", and the direction of rotation about the central axis 10a will be referred to as the "circumferential direction".

As shown in FIGS. 3A and 3B, the male luer 10 is a bar-shaped member that protrudes from the base 19. The outer circumferential face (i.e., side face) of the male luer 10 is a tapered face such that the outer diameter slightly decreases with increasing distance from the base 19 in the present embodiment. Note that the shape of the outer circumferential face of the male luer 10 is not limited to this, and any shape can be selected. For example, it may be a cylindrical face such that the outer diameter is constant in the up-down direction.

A channel 11 is formed in the male luer 10 along the lengthwise direction thereof. The channel 11 is not open at a tip face 10t of the male luer 10. Instead, a lateral hole 12 that is in communication with the channel 11 is formed in the vicinity of the tip of the male luer 10. The lateral hole 12 passes through the male luer 10 in the radial direction, and is open at two locations on the outer circumferential face of the male luer 10. Note that the lateral hole 12 may be open at only one location on the outer circumferential face of the male luer 10 instead of passing completely through male luer 10.

The configuration of the base 19 on the side opposite to the male luer 10 will not be described due to not being directly related to the present invention. Although the liquid channel 11 is open at the lower face of the base 19 in the present embodiment, the liquid channel 11 may be extended and put in communication with a desired channel.

A hood 20 is provided upright on the base 19 on the same side as the male luer 10 so as to surround the male luer 10. The hood 20 is shaped as a hollow cylinder that is coaxial with the male luer 10, and the height (up-down direction dimension) of the hood 20 is greater than the height of the male luer 10. The inner circumferential face of the hood 20 (the face opposing the male luer 10) is a cylindrical face having an inner diameter approximately the same as or slightly greater than the outer diameter of a female connector to which the male connector 1 of the present embodiment is to be connected. An opening (through-hole) 21 is formed in the hood 20. The opening 21 extends from the base 19 to a position slightly higher than the male luer 10. The opening 21 does not extend to the upper end of the hood 20, and a bridge portion 22 provided above the opening 21 connects portions of the hood 20 on the two sides of the opening 21 in the circumferential direction. An upper edge 20a of the hood 20 has a circular shape in a plan view, and is continuous in the circumferential direction with the same height.

A lock lever 30 is provided upright on the base 19 so as to oppose the male luer 10 via the opening 21 of the hood 20. The lock lever 30 includes an elastic portion 31 that extends perpendicularly from the base 19, a lock piece 33 provided on the upper end of the elastic portion 31, and a stopper 38 that extends from the lock piece 33 toward the base 19, and as shown in FIGS. 2B and 3A, the lock lever 30 is overall shaped as an upside "J" or an upside "U".

The elastic portion 31 is shaped as a thin plate that extends along a plane orthogonal to the radial direction of the male luer 10. As a result, the elastic portion 31 is capable of being displaced so as to elastically bend in a plane that includes the central axis 10a of the male luer 10.

The lock piece 33 is an approximately quadrangular plate-shaped member that extends along the radial direction of the male luer 10. The face of the lock piece 33 on the side opposing the male luer 10 is on the same plane as the elastic portion 31, and a claw 34 that protrudes toward the male luer 10 is formed on the upper end of this face of the lock piece 33. As shown in FIGS. 2B and 3A, the claw 34 includes an inclined face 34a and an engaging face 34b. The inclined face 34a is inclined so as to move away from the male luer 10 with increasing distance from the base 19. The engaging face 34b is arranged on the base 19 side relative to the inclined face 34a, and is a flat face that is approximately parallel to the horizontal direction. As shown in FIG. 2A, the apex portion of the claw 34 (the portion closest to the male luer 10) protrudes to a position on the male luer 10 side relative to the inner circumferential face of the hood 20.

The upper face of the lock piece 33 is an operation portion 35 that is sunken so as to be shaped as an approximately cylindrical face. The operation portion 35 extends and protrudes outward along the radial direction from the outer circumferential face of the hood 20.

The stopper 38 is elongated such that the face of the lock piece 33 on the side opposite to the male luer 10 extends toward the base 19. A lower end 38b of the stopper 38 and the base 19 are separated via a gap 39.

Figure 4:
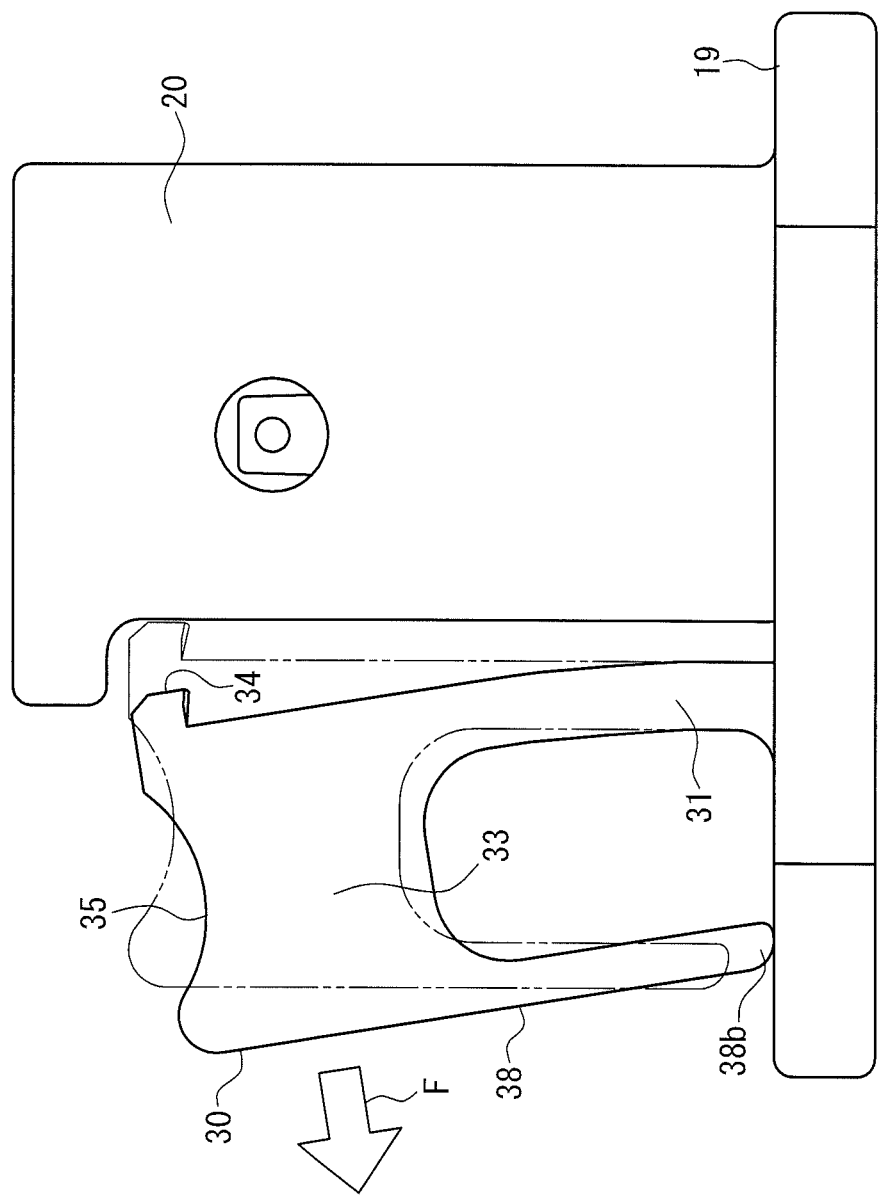
FIG. 4 is a side view of an elastically deformed lock lever in the male connector with a lock mechanism according to the embodiment of the present invention.

The lock lever 30 has a cantilever support structure in which the lower end of the elastic portion 31 fixed to the base 19 is the fixed end, and the upper end side provided with the claw 34 and the operation portion 35 is the free end. If a finger is brought into contact with the operation portion 35, and force F in a direction of separation from the hood 20 is applied to the operation portion 35, the elastic portion 31 undergoes elastic bending deformation, and the lower end 38b of the stopper 38 comes into contact with the base 19 as shown in FIG. 4. At this time, the claw 34 becomes displaced in a direction of separation from the male luer 10 approximately along the radial direction.

The hood 20 and the lock lever 30 described above configure the lock mechanism of the male connector 1 of the present embodiment.

It is preferable that the male luer 10, the base 19, the hood 20, and the lock lever 30 are made of a hard material. Specifically, the male luer 10, the base 19, the hood 20, and the lock lever 30 can be created with a method such as integral molding, using a resin material such as polyacetal, polycarbonate, polystyrene, polyamide, polypropylene, or rigid polyvinyl chloride.

The following describes operations of and a method of use of the male connector 1 of the present embodiment configured as described above.

Figure 5:
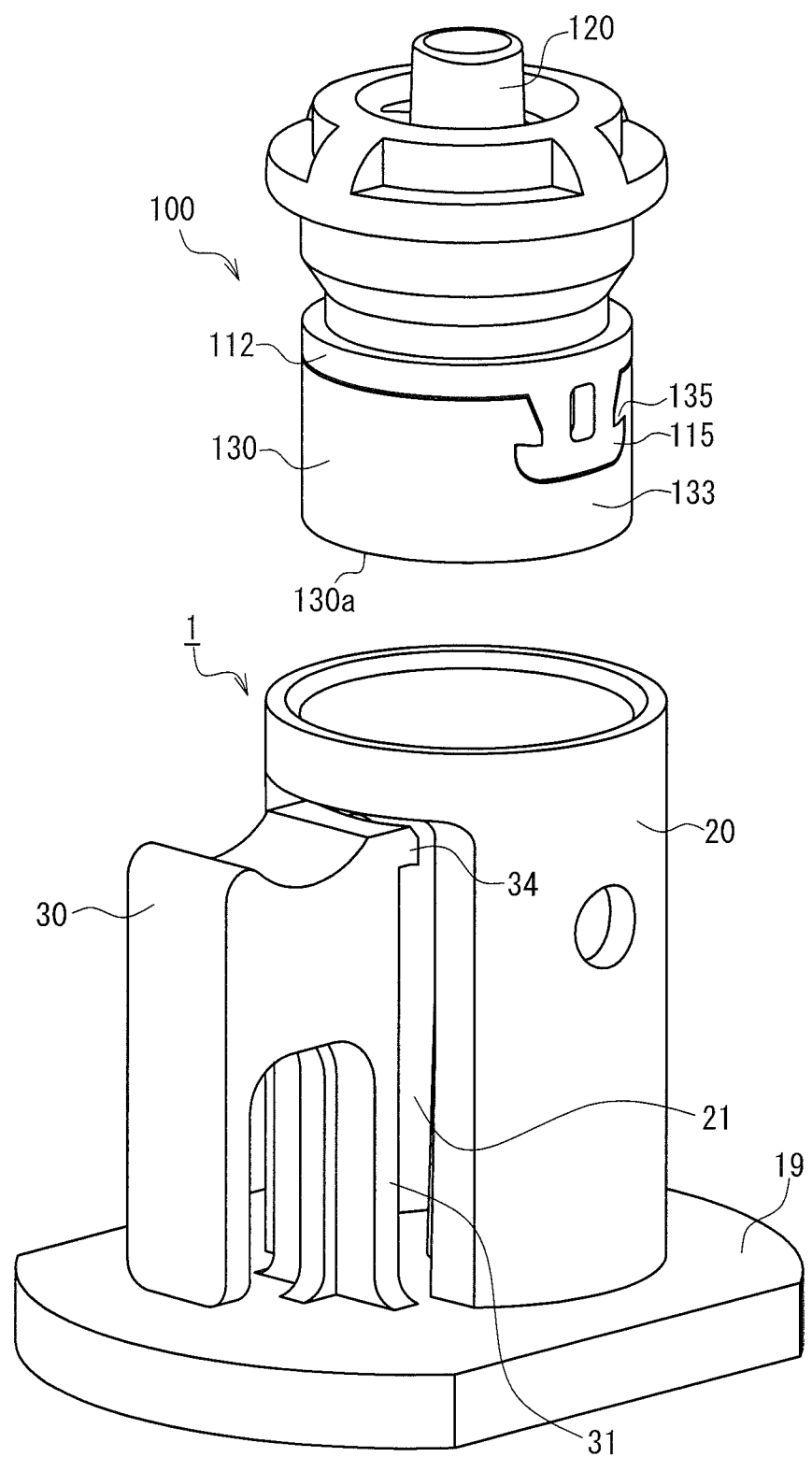
FIG. 5 is a perspective view of a female connector and the male connector with a lock mechanism according to the embodiment of the present invention immediately before connection.
Figure 6B:
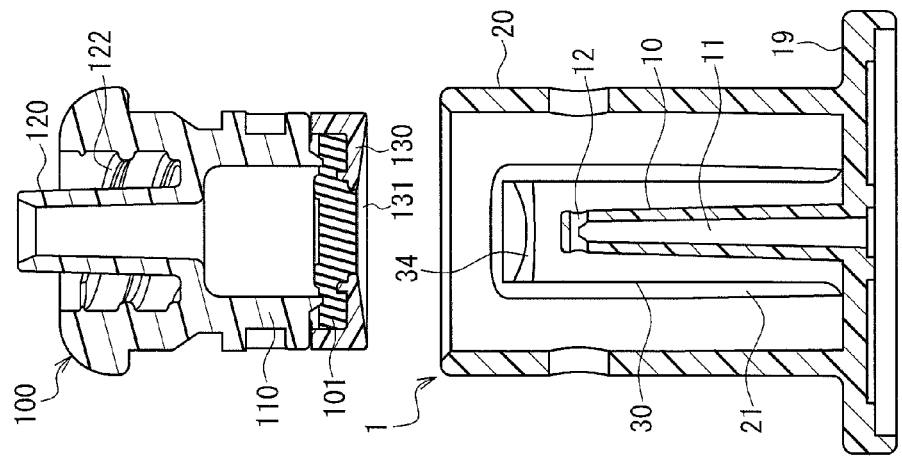
FIGS. 6A and 6B are cross-sectional views of the female connector and the male connector with a lock mechanism according to the embodiment of the present invention immediately before connection.
Figure 6A:
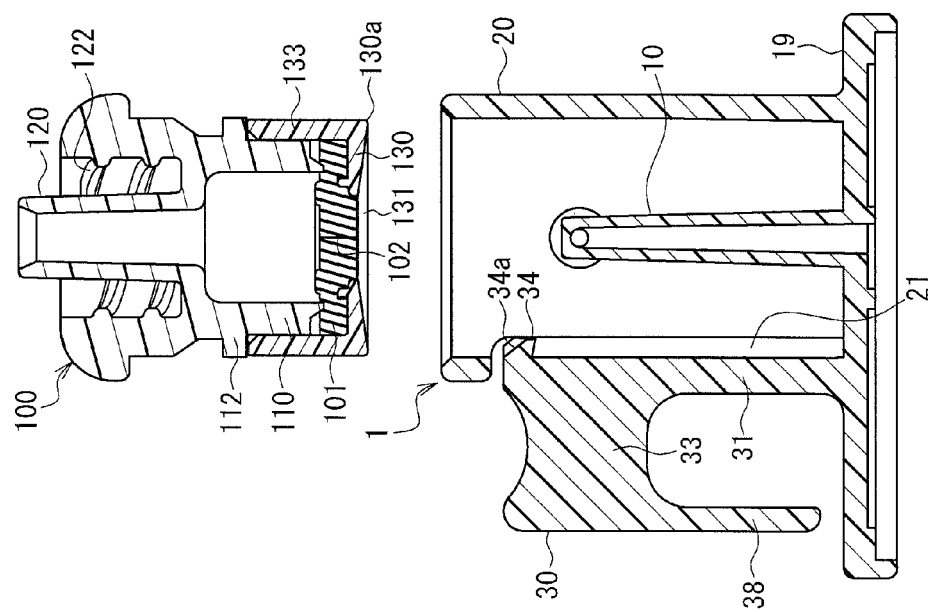

FIG. 5 is a perspective view of the male connector 1 and a needleless port 100 serving as the female connector, immediately before connection. FIGS. 6A and 6B are cross-sectional views of the male connector 1 and the needleless port 100 immediately before connection. The cross-sections in FIGS. 6A and 6B are the same as the cross-sections in FIGS. 3A and 3B respectively.

The needleless port 100 includes disk-shaped partition wall member (septum) 101 that is made of an elastic material such as rubber and is provided with a linear slit (incision) 102 in the central portion. The septum 101 is placed at the tip of a tubular base portion 110, and is covered by cap 130.

A locking claw 135 is formed by a notch in a cylindrical portion 133 encompassing the cap 130, and the cap 130 is fixed to the base portion 110 by engaging the locking claw 135 with a locking claw 115 formed on the outer circumferential face of the base portion 110. Accordingly, the septum 101 is sandwiched between the base portion 110 and the cap 130. An opening 131 is formed in the center of the cap 130, and the slit 102 in the septum 101 is exposed inside the opening 131. A protruding portion 112 is formed on the outer circumferential face of the base portion 110 on the side opposite to the septum 101, and protrudes so as to form a cylindrical face that is approximately the same as the cylindrical portion 133 of the cap 130. The protruding portion 112 is continuous in the circumferential direction of the base portion 110. A male luer 120 having a tapered outer circumferential face, and female threading 122 that is coaxial with the male luer 120 are provided on the side opposite to the base portion 110. Note that the configuration of the portions of the needleless port 100 on the side opposite to the base portion 110 are not limited to this, and these portions can have any configuration.

As shown in FIGS. 5, 6A, and 6B, the needleless port 100 is placed in opposition to the male connector 1. The cap 130 of the needleless port 100 is then inserted into the hood 20 of the male connector 1, and then the needleless port 100 is pushed toward the male connector 1. The tip of the male luer 10 then comes into contact with the septum 101 that is exposed inside the opening 131 of the cap 130, and enters the slit 102. At the same time, the inclined face 34a of the claw 34 of the lock lever 30 comes into contact with an outer edge 130a of the cap 130. While sliding over the inclined face 34a, the edge 130a of the cap 130 causes the elastic portion 31 to undergo deformation so as to elastically bend, and displaces the lock lever 30 in the direction in which the claw 34 moves away from the male luer 10. As the needleless port 100 enters the hood 20, the claw 34 slides over the cylindrical portion 133 of the cap 130 and the protruding portion 112 in the stated order. Then, when the claw 34 has completely passed the protruding portion 112, the elastic portion 31 undergoes elastic restoration, and the claw 34 and the protruding portion 112 engage with each other (enter a locked state).

Figure 7:
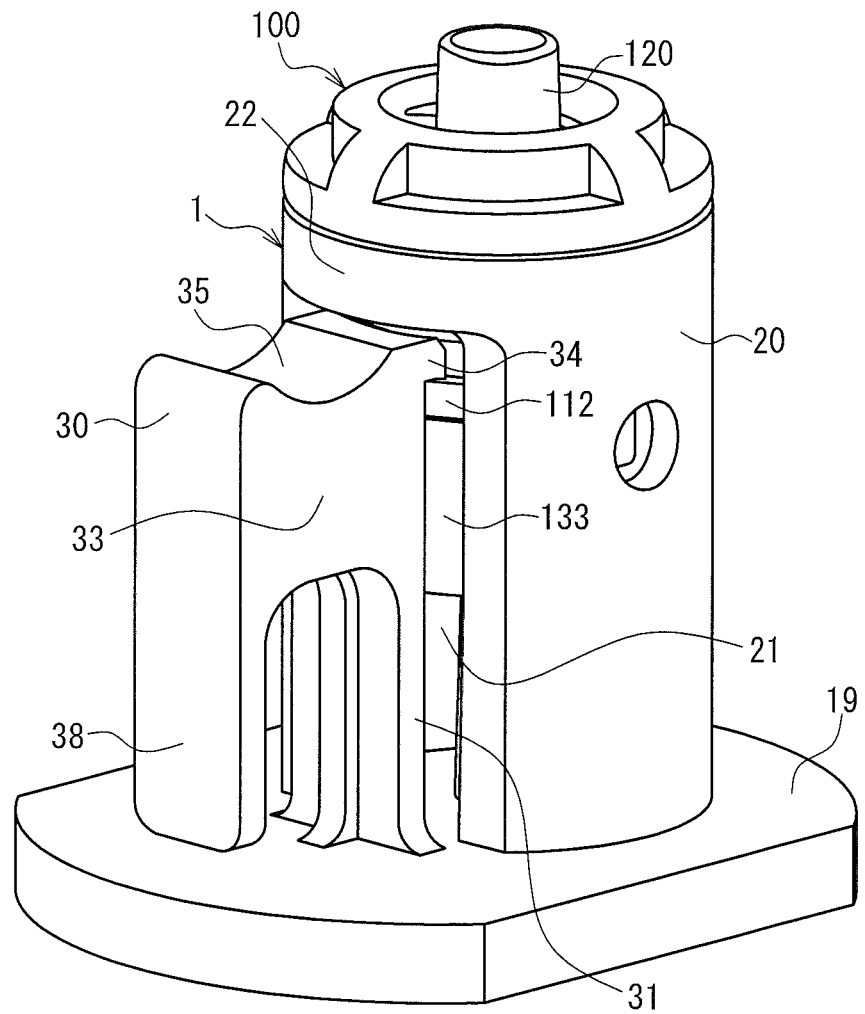
FIG. 7 is a perspective view of the female connector and the male connector with a lock mechanism according to the embodiment of the present invention, in which the connected state is locked by the lock mechanism.
Figure 8B:
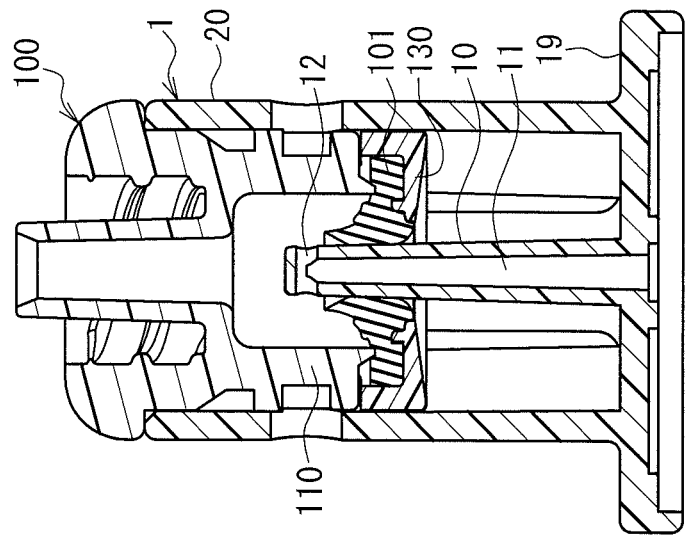
FIGS. 8A and 8B are cross-sectional views of the female connector and the male connector with a lock mechanism according to the embodiment of the present invention, in which the connected state is locked by the lock mechanism.
Figure 8A:
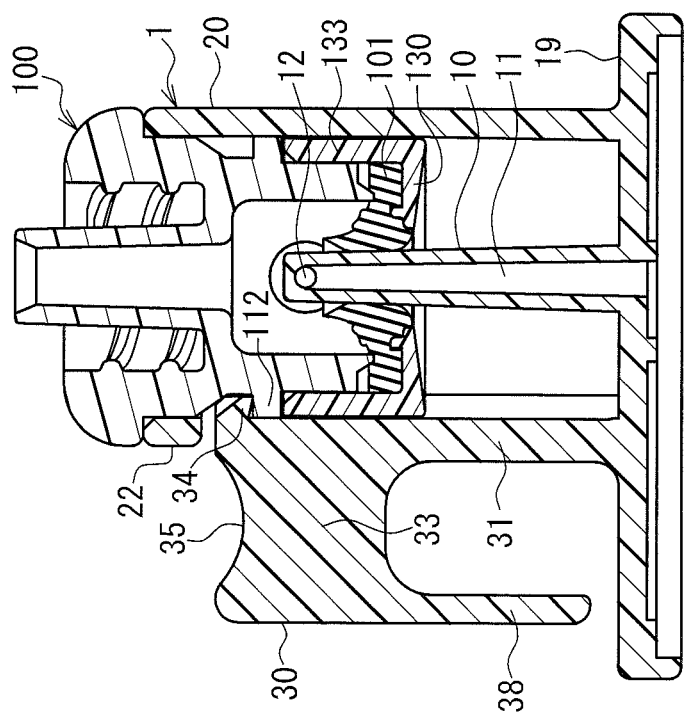
Figure 9A:
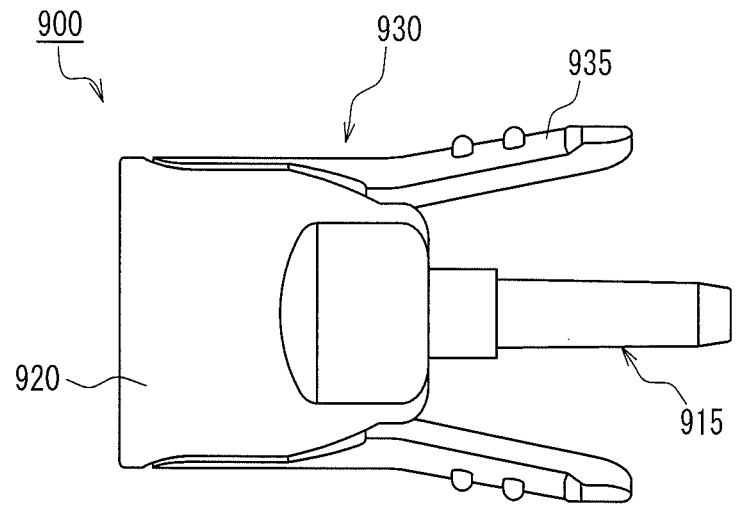
FIG. 9A is a side view of a conventional male connector with a lock mechanism.
Figure 9B:
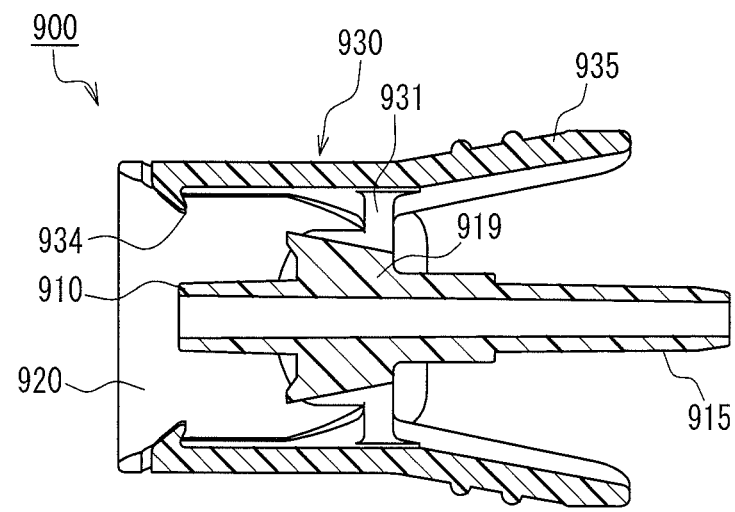
FIG. 9B is a cross-sectional view of the same.

FIG. 7 is a perspective view of the male connector 1 and the needleless port 100 in the connected and locked state. FIGS. 8A and 8B are cross-sectional views of the male connector 1 and the needleless port 100 in the connected and locked state. The cross-sections in FIGS. 8A and 8B are the same as the cross-sections in FIGS. 6A and 6B respectively.

The lock lever 30 is at approximately the same position as in the initial state (see FIGS. 1, 2A, 2B, 3A, and 3B), and the claw 34 thereof (particularly the engaging face 34b thereof (see FIGS. 2B and 3A)) is engaged with the protruding portion 112 of the needleless port 100. The male luer 10 has passed through the slit 102 in the septum 101, and thus the septum 101 is undergoing a large amount of elastic deformation. The openings of the lateral hole 12 in the male luer 10 are exposed inside the inner cavity of the base portion 110. In this state, a liquid can be caused to flow between the male luer 10 and the needleless port 100 via the channel 11 and the lateral hole 12.

The male connector 1 and the needleless port 100 can be separated by pressing a finger against the operation portion 35 of the lock lever 30 and displacing the lock lever 30 in the direction of separation from the hood 20 (see FIG. 4). The engagement between the claw 34 and the protruding portion 112 thus is canceled. If, at the same time, the needleless port 100 and the male connector 1 are pulled in the direction of separation from each other, the male connector 1 and the needleless port 100 can be separated. Immediately after the male luer 10 is withdrawn from the septum 101, the septum 101 undergoes elastic restoration, and the slit 102 closes.

As described above, according to the present embodiment, in the state where the male luer 10 has passed through the septum 101, the claw 34 of the male connector 1 engages with the protruding portion 112 of the needleless port 100. Accordingly, the male luer 10 is prevented from unintentionally coming out of the septum 101.

In order to cancel the engagement between the claw 34 and the protruding portion 112, it is necessary to displace the lock lever 30 in the direction of separation from the hood 20. With the conventional lock mechanism that includes the lock levers 930 (see FIG. 10), if pressing force F1 in the direction of approaching the tubular portion 915 is unintentionally applied to the operation portions 935, there is the possibility of the engagement between the claws 934 of the lock levers 930 and the needleless port 950 being canceled. In contrast, with the lock mechanism of the present embodiment, the engagement between the claw 34 and the protruding portion 112 is not canceled even if pressing force in the direction of approaching the male luer 10 is applied to any portion of the lock lever 30. Conversely, if force (pulling force) F in the direction of approaching the side opposite to the male luer 10 (see FIG. 4) unintentionally acts on the lock lever 30, there is the possibility of the engagement between the claw 34 and the protruding portion 112 being canceled. However, the possibility of this pulling force F acting on the lock lever 30 in actual use is very low compared to the possibility of pressing force in the opposite direction acting on the lock lever 30. Accordingly, the lock mechanism of the present embodiment is very safe and has a reduced possibility of the locked state being unintentionally canceled due to external force.

Since the claw 34 and the operation portion 35 are provided on the free end side of the lock lever 30, the direction in which the claw 34 needs to be moved in order to cancel the engagement between the claw 34 and the protruding portion 112 is the same as the direction of the force F (see FIG. 4) that needs to be applied to the operation portion 35 in order to move the claw 34 in the direction for canceling the engagement. Accordingly, the operation for canceling the locked state can be performed intuitively. Also, arranging the operation portion 35 at a position farther away from the fixed end of the lock lever 30 enables the amount of force F needed to cancel the engagement between the claw 34 and the protruding portion 112 to be reduced. Furthermore, arranging the claw 34 at a position farther from the fixed end of the lock lever 30 enables the displacement amount of the claw 34 to be increased.

Since only one lock lever 30 is provided, the locked state can be canceled with one finger, thus improving the ease of the operation for canceling the locked state. Also, the lower the number of lock levers 30 is, the lower the possibility of unintended external force acting on the lock lever 30 is. Accordingly, providing only one lock lever 30 reduces the possibility of the pulling force F for canceling the engagement between the claw 34 and the protruding portion 112 unintentionally acting on the lock lever 30, thus further improving safety.

With the conventional lock mechanism having a pair of lock levers 930 (see FIG. 10), two claws 934 engage with needleless port 900. Accordingly, the two claws 934 need to be disengaged from the needleless port 950 in order to cancel the locked state achieved by the lock levers 930.

However, even if the pressing force F1 is applied to the two operation portions 935 so as to widen the gap between the two claws 934, there are cases where the engagements of both of the two claws 934 to the needleless port 950 cannot be canceled at the same time. In this case, the engagements of the two claws 934 need to be canceled one at a time in order while the gap between the two claws 934 is widened. Accordingly, there has been the problem that the operation for canceling the locked state is cumbersome. In contrast, with the present embodiment, only one claw 34 for engagement with the needleless port 100 is provided, thus making it possible to cancel the locked state merely by applying the force F to the operation portion 35 so as to displace the lock lever 30. Accordingly, the operation for canceling the locked state is easy, and operability is improved.

Since the inclined face 34*a* is formed on the claw 34 on the side opposite to the base 19, in the process of connecting the male connector 1 and the needleless port 100, the operator can engage the claw 34 and the protruding portion 112 by merely pressing the needleless port 100 into the hood 20, without needing to touch the lock lever 30 with his/her hand. The ease of performing the connection operation is therefore favorable.

If the force F is applied to the operation portion 35 so as to displace the lock lever 30 in the direction of separation from the male luer 10, the lower end 38*b* of the stopper 38 comes into contact with the base 19, and thus the displacement of the lock lever 30 is limited. In this way, the stopper 38 of the lock lever 30 and the base 19 function as a displacement limiting means that limits the upper limit of the elastic displacement amount of the lock lever 30. The displacement limiting means prevents the operator from greatly displacing the lock lever 30 more than necessary when canceling the engagement between the claw 34 and the protruding portion 112, thus making it possible to prevent the elastic portion 31 from becoming plastically deformed or damaged by excessive bending deformation.

Since the hood 20 surrounds the male luer 10, there is a reduced possibility of the operator mistakenly touching the male luer 10 with his/her hand. This is advantageous in keeping the operator away from dangerous drug solutions and blood.

Furthermore, the hood 20 contributes to the positioning of the needleless port 100 in the horizontal plane as well. Specifically, the hood 20 positions the needleless port 100 relative to the male luer 10 such that the male luer 10 is precisely inserted into the slit 102 in the septum 101 that is exposed inside the opening 131 of the cap 130. Also, the hood 20 positions the needleless port 100 relative to the lock lever 30 such that the claw 34 reliably engages with the protruding portion 112, or such that the engagement between the claw 34 and the protruding portion 112 is reliably canceled.

The opening 21 for allowing the claw 34 to engage with the needleless port 100 is formed in the hood 20. If it only is necessary that the claw 34 provided on the lock lever 30 that is arranged outside the hood 20 engages with the needleless port 100 inside the hood 20, it is possible to apply a method of, for example, reducing the height (up-down direction dimension) of the hood 20 or forming a notch extending toward the base 19 in the upper edge 20*a* of the hood 20. However, the method of reducing the height of the hood 20 reduces the above-described functionality of the hood 20 (i.e., the separation function of preventing the operator from touching the male luer 10, and the function of positioning the needleless port 100). Also, the method of forming a notch in the edge 20*a* of the hood 20 reduces the mechanical strength of the edge 20*a* of the hood 20. The configuration of the present embodiment, in which the opening 21 is formed in the hood 20 and the claw 34 is engaged with the needleless port 100 via the opening 21, is advantageous in preventing the operator from mistakenly touching the male luer 10, in positioning the needleless port 100 using the hood 20, and in suppressing a reduction in the mechanical strength of the hood 20.

The opening 21 formed in the hood 20 does not extend to the upper end of the hood 20. The hood 20 includes the bridge portion 22 at a position higher than the opening 21. As a result, the upper edge 20*a* of the hood 20 is continuous in the circumferential direction with the same height. This improves the strength of the upper edge 20*a* of the hood 20. Accordingly, in the case where external force in the horizontal direction acts on the needleless port 100 in the locked state (FIGS. 7, 8A, and 8B), the hood 20 suppresses inclination and movement of the needleless port 100. This prevents the engagement between the claw 34 and the protruding portion 112 from being canceled by inclination or movement of the needleless port 100, thus further reducing the possibility of the locked state being unintentionally canceled, and further improving safety. Also, it is possible to prevent the hood 20 from being damaged by inclination or movement of the needleless port 100.

The channel 11 of the male luer 10 is not open at the tip face 10*t* of the male luer 10, and the lateral hole 12 in communication with the channel 11 is open at the outer circumferential face of the male luer 10. When the male luer 10 that has passed through the septum 101 is withdrawn from the septum 101 at a later time, liquid attached to the periphery of the openings of the lateral hole 12 is likely to be scraped away by the edges of the slit 102 in the septum 101, and therefore the above configuration is advantageous in reducing the amount of liquid that remains in the periphery of the openings of the lateral hole 12 after withdrawal from the septum 101.

The above embodiment is merely an illustrative example. The present invention is not limited to the above embodiment, and can be modified as appropriate.

As long as the lock lever 30 has a claw that engages with the needleless port 100 and an operation portion for displacing the lock lever 30 in order to cancel the locked state, the shape of the lock lever 30 can be changed as desired. For example, although the operation portion 35 is a concave curved face having an approximately cylindrical face shape in the above embodiment, the shape and position of the operation portion 35 can be set as desired as long as force F in the direction of separation from the male luer 10 (see FIG. 4) can be applied to the lock lever 30. For example, the operation portion 35 may be a protrusion for catching a finger, or a hole for the insertion of a finger. The stopper 38 may be omitted. Although the fixed end of the lock lever 30 is provided on the base 19, it may be provided on the hood 20.

Although the claw 34 is engaged with the protruding portion 112 of the needleless port 100 in the above embodiment, the portion of the needleless port that the claw 34 engages with may be changed appropriately according to the configuration of the needleless port. The shape and position of the claw 34 can be changed according to the portion for engaging with the needleless port.

The shape of the hood 20 is also not limited to the above embodiment. For example, if the needleless port 100 configures a coinfusion port (e.g., see Patent Document 1), a notch for avoiding interference with a tube connected to the coinfusion port may be formed in the upper edge 20*a* of the hood 20. Also, the opening 21 does not need to reach the base 19, and it may be a small opening to the extent that only the claw 34 can be inserted.

Although the lateral hole 12 of the male luer 10 extends along a straight line orthogonal to the central axis 10a (i.e., along the radial direction) in the above embodiment, the present invention is not limited to this, and it may extend along a straight line that intersects the central axis 10a at an angle other than a right angle. The number of lateral holes 12 is also not limited to the number in the above embodiment, and can be changed as desired. Also, a configuration is possible in which the lateral hole 12 is not formed, and the channel 11 is open at the tip face 10t of the male luer 10.

Although the female connector is the needleless port 100 including the septum 101 in the above embodiment, the present invention is applicable to a male connector that can be connected in a locked state to another female connector. For example, the female connector may be a rubber plug that seals the opening of a vial container. In this case, the male member is changed to a resin needle that has a sharp tip and a liquid channel and an air channel that are independent of each other, in place of the male luer 10. Also, the claw 34 of the lock lever 30 is changed so as to engage with a constricted portion formed at the mouth of the vial container.

A cover may be attached to the male member such that the opening of the channel on tip side of the male member is not exposed when the male member is not connected to a female connector. This cover is made of a flexible material having rubber elasticity, and when the male member is connected to a female connector, the cover undergoes elastic compression deformation while the male member passes through it (see Patent Documents 3 and 4).

The male connector with a lock mechanism of the present invention can be used in any application. The present invention is applicable as a male connector that is for connection to a drug solution bag and/or a vial container and is provided in a connector for connection to a vial container, a drug solution bag, and a syringe for moving a liquid between them (e.g., see Patent Documents 3 and 4).

INDUSTRIAL APPLICABILITY

Although there are no particular limitations on the field of use of the present invention, it can be used in a wide range as a male connector in which the state of connection to a female connector needs to be reliably maintained continuously. In particular, the present invention can be preferably used in medical field that handle dangerous drugs (e.g., anticancer drugs), blood, and the like. Furthermore, the present invention can be used in various types of fields that handle liquids for uses other than medical use, such as food substances.

DESCRIPTION OF REFERENCE NUMERALS

1 Male connector
10 Male luer (male member)
11 Channel
12 Lateral hole
20 Hood
20a Edge of hood
21 Opening
22 Bridge portion
30 Lock lever
31 Elastic portion
34 Claw
35 Operation portion
38 Stopper (displacement limiting means)
100 Needleless port (female connector)

The invention claimed is:
1. A male connector with a lock mechanism, comprising:
   a bar-shaped male member for insertion into a female connector; and
   a lock mechanism for maintaining a state in which the male member is inserted into the female connector,
   wherein
   the lock mechanism includes:
      a hood that is arranged so as to surround a periphery of the male member and is for insertion of the female connector;
      a single lock lever having a cantilever support structure capable of elastic displacement; and
      a base to which the hood and the lock lever are directly attached and from which the hood and the lock lever extend in the same direction,
   the lock lever includes:
      a fixed end at which the lock lever is fixed to the base;
      a free end that is an opposite side end of the fixed end of the lock lever;
      a claw that protrudes toward the male member to be engaged with the female connector;
      an operation portion that is provided on a same side as the free end relative to the fixed end; and
      an elastic portion that is capable of elastic bending deformation and is provided between the fixed end and the operation portion,
   an elongate opening is formed in the hood, a length of the opening extending parallel to the male member, the lock lever being located opposite to the male member via the opening,
   the claw is provided on a free end side of the lock lever relative to the elastic portion, and
   the lock lever is configured such that if the operation portion is displaced in a direction opposite to the male member, the elastic portion undergoes elastic bending deformation so as to increase a distance between the claw and the male member to cancel the engagement between the claw and the female connector.

2. The male connector with a lock mechanism according to claim 1, wherein a stopper of the lock lever and the base cooperate with each other to set an upper limit of an elastic displacement amount of the lock lever.

3. The male connector with a lock mechanism according to claim 1,
   wherein the opening is configured to allow engagement of the claw to the female connector.

4. The male connector with a lock mechanism according to claim 3,
   wherein the hood includes a bridge portion on a side on which the female connector is inserted relative to the opening, the bridge portion connecting portions of the hood that sandwich the opening in a circumferential direction.

5. The male connector with a lock mechanism according to claim 1,
   wherein a channel is formed in the male member, and a lateral hole in communication with the channel is open at an outer circumferential face of the male member.

6. The male connector with a lock mechanism according to claim 1, wherein the operation portion is configured to be activated by a force in a radially outward direction.

7. The male connector with a lock mechanism according to claim 1, wherein a free end of the cantilever support structure is not biased by another structural member of the lock mechanism in a radial direction.

* * * * *